United States Patent
Chen et al.

(10) Patent No.: US 9,840,474 B2
(45) Date of Patent: Dec. 12, 2017

(54) PYRIMIDINE COMPOUNDS AND USE AS ANTI-CERVICAL CANCER THEREOF

(71) Applicant: SICHUAN UNIVERSITY, Chengdu, Sichuan (CN)

(72) Inventors: Qianming Chen, Sichuan (CN); Yang He, Sichuan (CN); Hang Zhao, Sichuan (CN); Lu Jiang, Sichuan (CN)

(73) Assignee: SICHUAN UNIVERSITY, Chengdu, Sichuan (CN)

( * ) Notice: Subject to any disclaimer, the term of this patent is extended or adjusted under 35 U.S.C. 154(b) by 0 days.

(21) Appl. No.: 15/306,376

(22) PCT Filed: Apr. 24, 2014

(86) PCT No.: PCT/CN2014/076110
§ 371 (c)(1),
(2) Date: Oct. 24, 2016

(87) PCT Pub. No.: WO2015/161479
PCT Pub. Date: Oct. 29, 2015

(65) Prior Publication Data
US 2017/0044110 A1    Feb. 16, 2017

(51) Int. Cl.
*C07D 239/42*    (2006.01)
*A61K 31/505*    (2006.01)
*A61K 31/506*    (2006.01)

(52) U.S. Cl.
CPC .......... *C07D 239/42* (2013.01); *A61K 31/505* (2013.01); *A61K 31/506* (2013.01)

(58) Field of Classification Search
CPC .................................................. C07D 239/42
See application file for complete search history.

(56) References Cited

FOREIGN PATENT DOCUMENTS

| | | | |
|---|---|---|---|
| CN | 103058935 A | 4/2013 |
| JP | H08-134044 A | 5/1996 |
| JP | H10-212235 A | 8/1998 |
| TW | 200800919 A | 1/2008 |

*Primary Examiner* — Alexander R Pagano
*Assistant Examiner* — Ebenezer O Sackey
(74) *Attorney, Agent, or Firm* — Novick, Kim & Lee, PLLC; Allen Xue

(57) ABSTRACT

Provided is use of a pyrimidine compound or a pharmaceutically acceptable salt thereof in preparation of an anti-cervical cancer medicament. Research of the present invention has found that the above-mentioned pyrimidine compound can be effective against cervical cancer, and has a good inhibition effect on E6 and E7 of HPV16, and indicates that the above-mentioned pyrimidine compound also has a good anti-human papilloma virus effect, providing a new choice for clinical medication.

26 Claims, No Drawings

PYRIMIDINE COMPOUNDS AND USE AS ANTI-CERVICAL CANCER THEREOF

FIELD OF THE INVENTION

The present invention relates to new anti-cervical cancer uses of a pyrimidine compound.

BACKGROUND OF THE INVENTION

Cervical cancer is a malignant tumor frequently found in department of gynecology. For carcinoma in situ, the high incidence of age is 30-35 years old, while for infiltrating carcinoma, that is 45-55 years old. However, in recent years, the incidence has shown younger trend. In recent decades, the universal use of cervical cytological screening has allowed early detection on cervical cancer and precancerous lesion, and the incidence and the mortality of cervical cancer have obviously decreased. The occurrence of cervical cancer resulted from multifactor effects, and it is mainly related with infection of human papillomavirus (HPV), especially high risk HPV16 and 18, while other predisposing factors such as early marriage, early childbearing, multiple birth, excessive sexual partners, etc, are all causes of HPV infection. The study indicates 99.7% cervical cancers are caused by HPV infection. The said virus belongs to *Papillomavirus* genus of Papovaviridae family, with a diameter of 52-55 nm and without velamen. It possesses anicosahedron structure, with 72 capsids in its surface, and its viral genome is a double stranded and circular DNA molecules. It is anepitheliotropic virus, and widely distributes in human and animals, with high specificity. It has been known that HPV may induce benign tumors and nodules in human for a long time, such as human verruca vulgaris and condyloma acuminate growing in skin and mucous membrane close to reproductive organs, as well as papilloma growing in mucous membrane. The repeat infection of some HPVs that are high risk and do not have symptoms of nodules and so on might develop precancerous change, even invasive cancers.

According to homology of HPV, currently, more than 130 types have already been found. Based on its danger degree, these HPV viruses are classified as low risk (non-cancer relationship type) and high risk (cancer relationship type) types, in which high risk HPV types, that are correlated with genital tract precancerosis or cancers, are mainly HPV 16, 18, 31, 33, etc. Thus, development of drugs against HPV viruses also contributes to treatment of nodule or cancer conditions associated with HPV viruses. Patent application number 201310013707.1 disclosed a pyrimidine compound of formula 1 or pharmaceutically acceptable salts thereof:

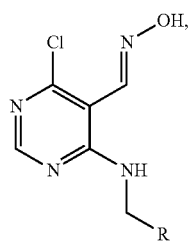

This patent application further reported this kind of compounds had certain anti-herpesvirus and anti-flu virus properties, and can be used for the treatment of infectious diseases correlated with varicella, herpes zoster, influenza, etc.

At present, reports on activities of this compounds against other tumors or viruses have not been found.

SUMMARY OF THE INVENTION

The object of the present invention is directed to provide new uses of a pyrimidine compound of formula 1.

The present invention provides the uses of a pyrimidine compound of formula 1 or a pharmaceutically acceptable salt thereof in preparation of an anti-cervical cancer medicament.

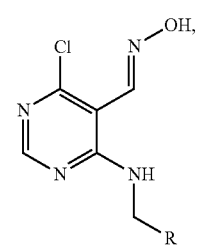

Wherein

R is selected from substituted or unsubstituted C4-10 aryl or heterocyclic aryl, in which, said substituents are selected from C1-6 alkyl, C1-4 alkoxyl, and C1-4 aminoalkyl or halogens.

Further, said cervical cancer is accompanied by infection of human papilloma virus, in which HPV is positive, but the cancerigenic reasons are possibly due to HPV, or due to other factors except for HPV infection.

More further, said cervical cancer is caused by human papilloma virus, in which HPV is positive, but the cancerigenic reasons are due to HPV infection.

Wherein, said human papilloma virus is high riskhuman papilloma virus.

Further, said high risk human papilloma virus is HPV16, HPV18, HPV31 or HPV33.

Still further, said highrisk human papilloma virus is HPV16.

Preferably, said medicament is an inhibitor of E6 or E7 proteins of HPV16.

Wherein, R is selected from substituted or unsubstituted C4-6 aryl or heterocyclic aryl, in which, said heterocyclic aryl is an oxygenous or nitrogenous group.

Further, said substituents are selected from C1-4 alkyl, C1-2 alkoxyl, C1-2 aminoalkyl, amino, or halogens.

More further, said compound is

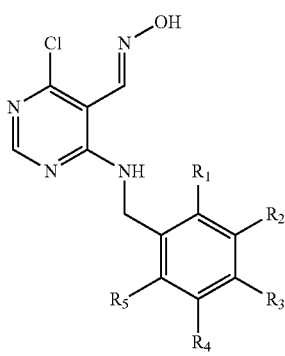

Wherein, $R_1$-$R_5$ are selected from C1-6 alkyl, C1-4 alkoxyl, C1-4 aminoalkyl, amino or H.

Wherein, $R_1$-$R_5$ are selected from C1-4 alkyl, C1-2 alkoxyl, C1-2 aminoalkyl, amino or H.

Further, $R_1$-$R_5$ are selected from C1-4 alkyl or C1-2 alkoxyl.

More further, $R_2$ and $R_4$ are H; $R_1$ and $R_5$ are H or C1-2 alkoxyl, but both of them can not simultaneously be H; $R_3$ is C1-4 alkyl.

Wherein, said C1-4 alkyl is butyl, C1-2 alkoxyl is methoxyl, and C1-2 aminoalkyl is aminomethyl. Further, said butyl is tert-butyl.

Preferably, said compound is:

4-(4-tert-butylbenzylamino)-5-formaldoxime-6-chloropyrimidine or 4-(2-methoxybenzylamino)-5-formaldoxime-6-chloropyrimidine.

At present, it is known that 99.7% cervical cancers are caused by HPV infection, and the present invention also showed above-mentioned compounds or a pharmaceutically acceptable salt thereof had an inhibitory effects on HPV found in cervical cancer. Thus, based on related experiments, the present invention further provides the uses of a pyrimidine compound of formula 1 or a pharmaceutically acceptable salt thereof in preparation of an anti-HPV medicament.

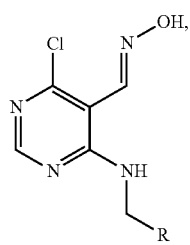

1

R is selected from substituted or unsubstituted C4-10 aryl or heterocyclic aryl, in which, said substituents are selected from C1-6 alkyl, C1-4 alkoxyl, C1-4 aminoalkyl or halogens.

Further, said human papilloma virus is high riskhuman papilloma virus.

Still further, said high risk human papilloma virus is HPV16, HPV18, HPV31 or HPV33.

Preferably, said high risk human papilloma virus is HPV16.

Further preferably, said medicament is an inhibitors of E6 or E7 proteins of HPV16.

Wherein, R is selected from substituted or unsubstituted C4-6 aryl or heterocyclic aryl, in which, said heterocyclicaryl is an oxygenous or nitrogenous group.

Further, said substituents are selected from C1-4 alkyl, C1-2 alkoxyl, C1-2 aminoalkyl, amino, or halogens.

More further, said compound is

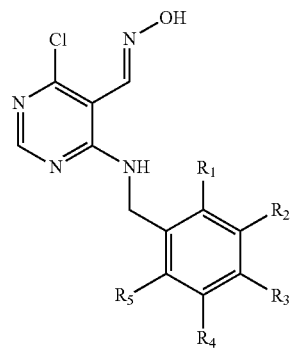

2

Wherein, $R_1$-$R_5$ are selected from C1-6 alkyl, C1-4 alkoxyl, C1-4 aminoalkyl, amino or H.

Wherein, $R_1$-$R_5$ are selected from C1-4 alkyl, C1-2 alkoxyl, C1-2 aminoalkyl, amino or H.

Further, $R_1$-$R_5$ are selected from C1-4 alkyl or C1-2 alkoxyl.

More further, $R_2$ and $R_4$ are H; $R_1$ and $R_5$ are H or C1-2 alkoxyl, but both of them can not simultaneously be H; $R_3$ is C1-4 alkyl.

Wherein, said C1-4 alkyl is butyl, C1-2 alkoxyl is methoxyl, and C1-2 aminoalkyl is aminomethyl.

Further, said butyl is tert-butyl.

Preferably, said compound is:

4-(4-tert-butylbenzylamino)-5-formaldoxime-6-chloropyrimidine or 4-(2-methoxybenzylamino)-5-formaldoxime-6-chloropyrimidine.

The "pharmaceutically acceptable salt" in the present invention includes nontoxic salts of general formula 1 or 2 for living organisms, and contains salts formed by compounds of the present invention with hydrochloric acid, hydrobromic acid, nitric acid, sulphuric acid, phosphoric acid, citric acid, malic acid, formic acid, maleic acid, acetic acid, malonic acid, pamoic acid, 1,5-naphthalene disulfonic acid, cyclohexylaminosulfonic acid, salicylic acid, adipic acid, glutaric acid, vanillic acid, oxaloacetic acid, ascorbic acid, lactic acid, fumaric acid, succinic acid, tartaric acid, methanesulfonic acid or p-toluene sulfonic acid, etc., respectively, as well as salts formed by compounds of the present invention with alkali that contain sodium, potassium, magnesium, zinc, or iron, etc., but the salts are not limited to those mentioned.

In one embodiment of the present invention, isotope-labeled above compounds or their pharmaceutically acceptable salts are also included, and said isotope-labeled compounds mean the same compounds with those listed, but one or more atoms of them are substituted by other atoms, in which the atomic mass or the mass number is different from those commonly found in nature. The isotope that can be introduced in compounds includes hydrogen, carbon, nitrogen, oxygen, sulphur, i.e. 2H, 3H, 13C, 14C, 15N, 17O, 18O, 35S. The compounds containing above isotopes and/or other atom isotopes and their stereoisomers, as well as a pharmaceutically acceptable salt thereof, are also included in the scope of the present invention.

Besides said compounds according to the present invention and their pharmaceutically acceptable salts, the related pharmaceutical uses of prodrugs of these compounds should also be included in the protective scope of the present invention, in which said prodrug means the active constituent that is released by in vivo enzymatic or non-enzymatic conversion of compounds and then play efficacy, and said compounds are obtained by structural modification of pyrimidine compounds according to the present invention.

The investigation according to the present invention indicates that said pyrimidine compounds can be effective against cervical cancer, and have an good inhibitory effect on HPV16 E6 and E7, suggesting that said pyrimidine compounds also have a good anti-human papilloma virus effect, and provide a potent candidate for clinical medication.

Obviously, according to above-mentioned content of the present invention and using common technical knowledge and means in the art, diverse kinds of modification, replacement or variation can further be made, without departing from above basic technical idea of the present invention.

The following examples are provided to further illustrate above content of the present invention, but it should not be understood that the object scope of present invention is limited to following examples. The techniques accomplished via above content of the present invention all belong to the scope of the present invention.

EXAMPLES

Example 1 Effects of CH01 and CH02 on Human Cervical Carcinoma Caski Cells and HPV16 Viruses

[Experimental Object]

In order to investigate in vitro effects of CH01 and CH02 against cervical cancer and HPV16 viruses, in the experiment, the cytotoxicity of above compounds, together with their effects on HPV16 E6 and E7 mRNA, is investigated by culture with human cervical cancer cells (HPV16 positive). Structures of test compounds are shown as follows:

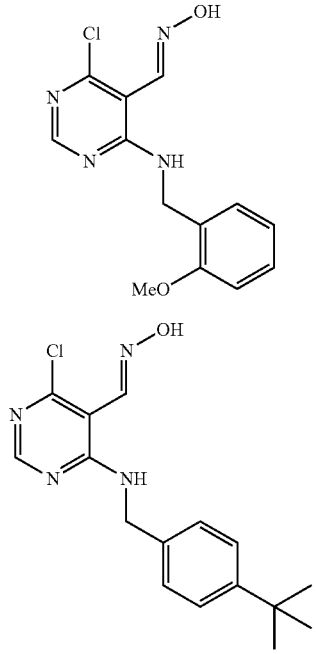

Test compounds of the present invention were prepared as the methods of patent application number 201310013707.1.

[Experimental Method]

1. Cytotoxicity: MTT method was used, and Reed-Muench method was used to calculate indexes median toxic concentration ($TC_{50}$) and maximum non-toxic concentration ($TC_0$).
2. HPV16 E6 and E7 mRNA: The cell culture was treated for 48 h at maximum non-toxic concentration, and then the culture was terminated. Total RNA in cells was extracted, and effects of test samples on HPV16 E6 and E7 mRNA were measured using Real-time PCR method.

[Experimental Result]

1. Inhibition Test of Cervical Cancer Caski Cells

TABLE 1

| Concentration (µg/ml) | CH01 OD | CH01 cell survival rate % | CH02 OD | CH02 cell survival rate % |
|---|---|---|---|---|
| 200 | 0.437333 | 0.457571 | 0.555667 | 0.624004 |
| 100 | 0.296667 | 0.259728 | 0.375667 | 0.370839 |
| 50 | 0.28 | 0.236287 | 0.308667 | 0.276606 |
| 25 | 0.283 | 0.240506 | 0.280333 | 0.236756 |
| 12.5 | 0.303333 | 0.269105 | 0.274333 | 0.228317 |
| 6.25 | 0.411667 | 0.421472 | 0.272667 | 0.225973 |
| 3.125 | 0.466667 | 0.498828 | 0.294333 | 0.256446 |
| 1.5625 | 0.488 | 0.528833 | 0.313 | 0.2827 |
| 0.78125 | 0.566667 | 0.639475 | 0.383667 | 0.382091 |
| 0.390625 | 0.635333 | 0.736053 | 0.473333 | 0.508204 |
| 0.195313 | 0.784667 | 0.946085 | 0.78 | 0.939522 |
| 0.097656 | 0.836667 | 1.019222 | 0.835667 | 1.017815 |
| CC | 0.112333 | | | |
| blank | 0.823333 | | | |

Results in above table showed compounds had good inhibitory effects on cervical cancer cells, and the $IC_{50}$ value of sample CH01 is about 1.5 µg/ml, while the $IC_{50}$ value of sample CH02 is about 0.4 µg/ml.

In addition, the experiment of the present invention confirmed compounds had inhibitory effects on the cervical cancer cells, and the cervical cancer cells were positive to HPV16, suggesting above compounds might have inhibitory effect on HPV viruses.

2. Effects of Samples on Expression of HPV16 E6 mRNA and HPV16 E7 mRNA in Caski Cells

| | Concentration (µg/ml) | E6 One independent tests (inhibitory rate) | E6 Two independent tests (inhibitory rate) | E7 One independent tests (inhibitory rate) | E7 Two independent tests (inhibitory rate) |
|---|---|---|---|---|---|
| CH01 | 0.2 | 0.577 | 0.553 | 0.484 | 0.449 |
| | 0.067 | 0.489 | 0.494 | 0.488 | 0.455 |
| CH02 | 0.2 | 0.599 | 0.549 | 0.516 | 0.526 |
| | 0.067 | 0.461 | 0.481 | 0.484 | 0.488 |
| cidofovir | 0.2 | 0.326 | 0.336 | 0.321 | 0.324 |

[Experimental Results]
1. CH01 showed inhibitory effects on HPV E6 and E7 mRNA in Caski cells.
2. CH02 showed inhibitory effects on HPV E6 and E7 mRNA in Caski cells.

E6 and E7 are two important proteins for expression of HPV16 viruses, and both of proteins can activate protooncogene P53 in cells, resulting in cancerzation of cells. At present, a large number of literature researches indicated inhibition of HPV16 E6 and E7 proteins might inactivate protooncogene P53 and produce anti-tumor effects. The experimental results showed CH01 and CH02 had good inhibitory activity on E6 and E7 proteins, with a better inhibitory activity than the positive control cidofovir, indicating that compounds provided in the present invention might inhibit viral activity by suppression of E6 and E7 proteins in HPV and thus realized effects against cervical cancer (HPV positive).

Combined with above-mentioned results, it is known that pyrimidine compounds according to the present invention have good effect against cervical cancer, and have an inhibitory effect on HPV16 E6, E7, and so on, that are closely related with cancers. Said pyrimidine compounds show good physiological activity and provide a potent candidate for clinical medication.

The invention claimed is:

1. An anti-cervical cancer medicament, comprising a pyrimidine compound of formula 1 or a pharmaceutically acceptable salt thereof,

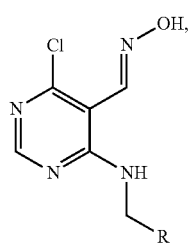

1 wherein R is chosen from substituted or unsubstituted C4-10 aryl or heterocyclic aryl, in which, said substituents are chosen from C1-6 alkyl, C1-4 alkoxyl, C1-4 aminoalkyl or halogens.

2. The medicament according to claim 1, wherein said cervical cancer is in presence of an infection by human papilloma virus.

3. The medicament according to claim 2, wherein said cervical cancer is caused by human papilloma virus.

4. The medicament according to claim 3, wherein said human papilloma virus is HPV16, HPV18, HPV31 or HPV33.

5. The medicament according to claim 1, wherein said medicament is an inhibitor of E6 and/or E7 proteins in HPV16.

6. The medicament according to claim 1, wherein R is chosen from substituted or unsubstituted C4-6 aryl or heterocyclic aryl, in which, said heterocyclic aryl is an oxygenous or nitrogenous group.

7. The medicament according to claim 1, wherein said substituents are chosen from C1-4 alkyl, C1-2 alkoxyl, C1-2 aminoalkyl, amino, or halogens.

8. A pyrimidine compound of formula 2

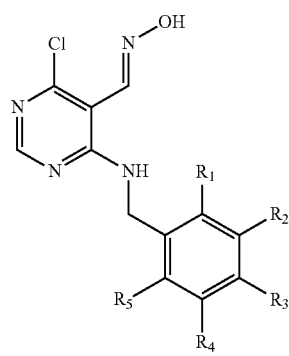

2 wherein $R_1$ to $R_5$ are chosen from C1-6 alkyl, C1-4 alkoxyl, C1-4 aminoalkyl, amino or H.

9. The pyrimidine compound according to claim 8, wherein $R_1$ to $R_5$ are chosen from C1-4 alkyl, C1-2 alkoxyl, C1-2 aminoalkyl, amino or H.

10. The pyrimidine compound according to claim 9, wherein $R_1$ to $R_5$ are chosen from C1-4 alkyl or C1-2 alkoxyl.

11. The pyrimidine compound according to claim 10, wherein $R_2$ and $R_4$ are H; $R_1$ and $R_5$ are chosen from H or C1-2 alkoxyl with the proviso that $R_1$ and $R_5$ are not simultaneously H; and $R_3$ is C1-4 alkyl.

12. The pyrimidine compound according to claim 9, wherein said C1-4 alkyl is butyl, C1-2 alkoxyl is methoxyl, and C1-2 aminoalkyl is aminomethyl.

13. The pyrimidine compound according to claim 12, wherein said butyl is tert-butyl.

14. The medicament according to claim 1, wherein said compound is: 4-(4-tert-butylbenzylamino)-5-formaldoxime-6-chloropyrimidine or 4-(2-methoxybenzylamino)-5-formaldoxime-6-chloropyrimidine.

15. A method of inhibiting human papilloma virus (HPV), comprising administering a medicament containing a pyrimidine compound of formula 1 or a pharmaceutically acceptable salt thereof to a patient in need thereof,

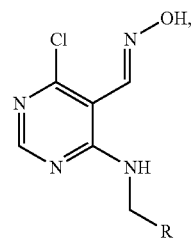

1 wherein R is chosen from substituted or unsubstituted C4-10 aryl or heterocyclic aryl, in which, said substituents are chosen from C1-6 alkyl, C1-4alkoxyl, C1-4 aminoalkyl or halogens.

16. The method according to claim 15, wherein said high-risk human papilloma virus is HPV16, HPV18, HPV31 or HPV33.

17. The method according to claim 15, wherein said medicament is an inhibitor of E6 and/or E7 proteins in HPV16.

18. The method according to claim 15, wherein R is chosen from substituted or unsubstituted C4-6 aryl or heterocyclic aryl, in which, said heterocyclic aryl is an oxygenous or nitrogenous group.

19. The method according to claim 15, wherein said substituents are chosen from C1-4 alkyl, C1-2 alkoxyl, C1-2 aminoalkyl, amino, or halogens.

20. The method according to claim 15, wherein said compound is

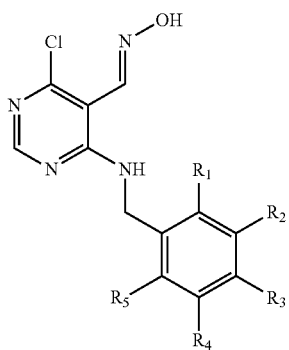

wherein $R_1$ to $R_5$ are chosen from C1-6 alkyl, C1-4 alkoxyl, C1-4 aminoalkyl, amino or H.

21. The method according to claim 20, wherein $R_1$ to $R_5$ are chosen from C1-4 alkyl, C1-2alkoxyl, C1-2aminoalkyl, amino or H.

22. The method according to claim 21, wherein $R_1$ to $R_5$ are chosen from C1-4 alkyl or C1-2alkoxyl.

23. The method according to claim 22, wherein $R_2$ and $R_4$ are H; $R_1$ and $R_5$ are H or C1-2 alkoxyl with the proviso that $R_1$ and $R_5$ are not simultaneously H; and $R_3$ is C1-4 alkyl.

24. The method according to claim 21, wherein said C1-4 alkyl is butyl, C1-2 alkoxyl is methoxyl, and C1-2 aminoalkyl is aminomethyl.

25. The method according to claim 24, wherein said butyl is tert-butyl.

26. The method according to claim 15, wherein said compound is: 4-(4-tert-butylbenzylamino)-5-formaldoxime-6-chloropyrimidine or 4-(2-methoxybenzylamino)-5-formaldoxime-6-chloropyrimidine.

* * * * *